United States Patent [19]

Yoko et al.

[11] Patent Number: 4,487,762

[45] Date of Patent: Dec. 11, 1984

[54] ANTIBIOTIC 5057B SUBSTANCE

[75] Inventors: Kusakabe Yoko; Mizuno Taku, both of Tokyo, Japan

[73] Assignee: Kaken Chemical Co. Ltd., Japan

[21] Appl. No.: 403,491

[22] PCT Filed: Nov. 6, 1981

[86] PCT No.: PCT/JP81/00320

§ 371 Date: Jul. 13, 1982

§ 102(e) Date: Jul. 13, 1982

[87] PCT Pub. No.: WO82/01707

PCT Pub. Date: May 27, 1982

[30] Foreign Application Priority Data

Nov. 13, 1980 [JP] Japan .................................. 55-158856

[51] Int. Cl.$^3$ .......................... A61K 35/74; C12P 1/06
[52] U.S. Cl. ..................................... 424/120; 435/169
[58] Field of Search ........................ 424/120; 435/169

[56] References Cited

FOREIGN PATENT DOCUMENTS 8641 4/1979 Japan ................................... 424/122

Primary Examiner—Jerome D. Goldberg
Attorney, Agent, or Firm—Jacobs & Jacobs

[57] ABSTRACT

New antibiotic 5057B and process for its preparation. Antibiotic 5057B itself is an acidic material, and its sodium salt has the following physical and chemical properties:

(1) Colorless needles
(2) Melting point: 143°–145° C.
(3) Elementary analysis (Found %): C, 59.96; H, 9.03; O, 27.60; Na, 3.41
(4) Specific rotation: $[\alpha]_D^{25} = +5.5°$ (C 1, CHCl$_3$)
(5) Maximum absorption in ultraviolet absorption spectrum: $\lambda_{max}^{MeOH}(E_{1\ cm}^{1\%})$ 290 nm (0.88)
(6) Characteristic absorption (cm$^{-1}$) in infrared absorption spectrum (taken with the potassium bromide tablet: 3480, 3000, 2970, 2812, 1719, 1645, 1595, 1465, 1385, 1160, 1100, 1035, 980
(7) Solubility: soluble in methanol, ethanol, ethyl acetate, chloroform, ether, acetone, and benzene and so forth; insoluble in water
(8) Color reaction: positive in the 2,4-dinitrophenylhydrazine reaction; negative in the ninhydrin reaction and the vanilline-sulfuric acid reaction; colors with I$_2$ gas.

The antibiotic is prepared by culturing Streptomyces bacteria, and collecting the antibiotic from the culture product.

2 Claims, 3 Drawing Figures

ANTIBIOTIC 5057B SUBSTANCE

FIELD OF THE INVENTION

The present invention relates to a new antibiotic 5057B substance and a process for production thereof.

DESCRIPTION OF THE PRIOR ART

The present inventors previously found that an actinomycete Streptomyces sp. 5057 strain belonging to the genus Streptomyces (FERM BP-62) produces a substance having an antibacterial activity in its culture broth and isolated an antibiotic 5057(A) from the culture broth (refer to the specification of Japanese Patent Publication No. 8641/1979).

The present inventors, in the course of further researches, have found that a new substance different from the 5057A substance is present in said culture broth and isolated the same, which was designated as the 5057B substance.

The 5057B substance, in view of its physicochemical and biological properties, is an antibiotic belonging to the antibiotic group of polyether series. Among antibiotics of polyether series, there are heretofore known, as those showing ultraviolet absorption in the vicinity of 290 nm, lysocellin (The Journal of Antibiotics, Vol. 28, Pages 118–121, 1975) and the 5057A substance (Japanese Patent Publication No. 8641/1979); however, the 5057B substance is a new antibiotic which differs from the above-mentioned known antibiotics in the melting point, specific rotation, infrared absorption spectrum, and the Rf value on silica gel thin layer chromatography.

DISCLOSURE OF THE INVENTION

The present invention relates to a new antibiotic 5057B substance having a potent antibacterial activity, especially against gram-positive bacteria, and a process for production thereof comprising cultivating a microoragnism, belonging to the genus Streptomyces, which has the ability to produce the 5057B substance and then recovering the 5057B substance from the culture broth.

The strain Streptomyces sp. 5057, belonging to the genus Streptomyces, employed in the production of the 5057B substance was deposited on May 1, 1981 with Fermentation Research Institute, Agency of Industrial Science and Technology (No. 1-3, Yatabechohigashi 1-chome, Tsukuba District, Ibaragi Prefecture, Japan) and accorded the accession number FERM BP-62. Microbiological properties of the strain is described in detail in the specification of Japanese Patent Publication No. 8641/1979.

In order to obtain the 5057B substance according to the present invention, ordinary methods for cultivation of actinomycetes can be employed, but a cultivation with aeration-agitation is suited for the industrial production. The cultivation temperature of 25°–35° C. is usual, but the temperature of 30° C. is preferable. As a culture medium, there can be used one customarily employed for cultivation of microoragnisms belonging to the genus Streptomyces, for example, one containing carbon sources such as glucose, starch, glycerol, dextrin, sucrose, and animal or vegetable oils and nitrogen sources such as soybean meal, corn steep liquor, wheat embryo, and ammonia. Further, if necessary, inorganic salts such as calcium carbonate, sodium chloride, potassium chloride, and phosphates can be added; it is also possible to suitably add organic or inorganic salts having an action to assist the growth of the microoragnism and encourage the production of the 5057B substance. The accumulation of the 5057B substance produced reaches the maximum usually 4–8 days after the start of the cultivation in both cases of shaking and tank cultures.

The 5057B substance is recovered from the culture broth by utilizing its physiochemical properties; since the substance is lipo-soluble and acidic, there can be used, in a suitable combination, extraction with a variety of organic solvents, chromatography on a variety of activated adsorbents, and other methods. For example, an isolation method consisting of a combination of extraction and chromatography is carried out as follows: The culture broth, after addition of a filter aid such as diatomaceous earth and Radiolite 700 and the like, is filtered, and the filtrate and the microbial cells are each extracted with suitable solvents such as ethyl acetate and acetone. The cell extract and the filtrate extract are combined. Evaporation of the solvent from the combined extracts leaves, as the residue, crude crystals of a mixture of the 5057B and 5057A substances. The mixture is subjected to, for example, chromatography to isolate the 5057B substance from the mixture. The eluate is concentrated under reduced pressure and then the residue treated, in a suitable solvent, for example ethyl acetate, with a dilute hydrochloric acid solution and then with a dilute sodium carbonate solution and so on to afford crystals of sodium salt of the 5057B substance. Recrystallization of the crystals from a suitable solvent such as n-hexane-ethyl acetate gives pure sodium salt of the 5057B substance.

Properties of the sodium salt of the 5057B substance thus obtained are as follows:

(1) Colorless needles (the 5057B substance itself is acidic)

(2) Melting point: 143°–145° C.

(3) Elementary analysis (Found %): C, 59.96; H, 9.03; O, 27.60; Na, 3.41.

(4) Specific rotation: $[\alpha]_D^{25} = +5.5°$ (C 1, CHCl$_3$)

(5) Ultraviolet absorption spectrum: The absorption spectrum taken in a 0.25% methanol solution is shown in FIG. 1. Maximum absorption: $\lambda_{max}^{MeOH}$ (E$_{1\ cm}^{1\%}$) 290 nm (0.88)

(6) Characteristic absorption (cm$^{-1}$) in infrared absorption spectrum (taken with the potassium bromide tablet): 3480, 3000, 2970, 2812, 1719, 1645, 1595, 1465, 1385, 1160, 1100, 1035, 980 The infrared absorption spectrum is shown in FIG. 2.

(7) Nuclear magnetic resonance spectrum (taken in CDCl$_3$) Proton NMR spectrum is shown in FIG. 3.

(8) Solubility: soluble in methanol, ethanol, ethyl acetate, chloroform, ether, acetone, and benzene and so on; insoluble in water (9) Color reaction: positive in the 2,4-dinitrophenylhydrazine reaction; positive in the ninhydrin reaction and the vanillinesulfuric acid reaction; colors with I$_2$ gas

(10) Thin layer chromatography silica gel: Kieselgel GF$_{254}$ manufactured by Merck Co.

| Solvent system | Rf value |
| --- | --- |
| chloroform-methanol (20:1) | 0.30 |
| ethyl acetate-methanol (20:1) | 0.64 |
| n-hexane-ethyl acetate (1:2) | 0.62 |

| Solvent system | Rf value |
|---|---|
| benzene-ethyl acetate (1:1) | 0.37 |

(11) The antibacterial spectrum is shown in the following table:

| Test microrganism | Minimum inhibitory concentration (mcg/ml) | Medium |
|---|---|---|
| Staphylococcus aureus FDA 209 PJC-1 | 0.5 | a |
| Staphylococcus aureus resistant to penicillins, streptomycin, kanamycin, chloramphenicol, and tetracyclines | 0.5 | a |
| Bacillus subtilis ATCC-6636 | 0.5 | a |
| Sarcina lutea NIHJ | 2 | a |
| Micrococcus luteus ATCC-398 | 0.5 | a |
| Mycobacterium smegmatis ATCC-607 | 5 | a |
| Mycobacterium tuberculosis $H_{37}R_v$ | 10 | b |
| Escherichia coli NIHJ JC-2 | 100 | a |
| Escherichia coli resistant to streptomycin, kanamycin, chloramphenicol, and tetracyclines | 100 | a |
| Klebsiella pneumoniae GN-6445 | 100 | a |
| Proteus vulgaris GN-75 | 100 | a |
| Pseudomonas aeruginosa IFO-3756 | 100 | c |
| Penicillium citrinum ATCC-9849 | 100 | c |
| Aspergillus fumigatus NI-5561 | 100 | c |
| Alternaria kikuchiana CBS | 100 | c |
| Ophiobolus miyabeanus ITO | 50 | c |
| Nocardia asteroides | 5 | d |
| Candida albicans | 50 | d |

In the table, the sign a means the heart infusion agar medium, the sign b the Kirchner's semifluid agar medium, the sign c the potato-sucrose agar medium, and the sign d the Sabouraud's 3% glucose agar medium. As can be seen from the antibacterial spectrum, the 5057B substance exhibits a potent antibacterial activity especially against gram-positive microorganisms.

(12) Acute toxicity test Acute toxicity tests were performed with mice. As a result, the $LD_{50}$ value was 50 mg/kg in the case of the intraperitoneal administration and 500 mg/kg or more in the case of the oral adminstration.

Melting points, specific rotations and Rf values on silica gel thin layer chromatography of the 5057A and 5057B substances are shown in the following table:

|  | 5057A substance (as the Na salt) | 5057B substance (as the Na salt) |
|---|---|---|
| Melting point | 133-135° C. | 143-145° C. |
| Specific rotation | +1.0 (C 1, MeOH) | +5.5 (C 1, CHCl$_3$) |
| Rf value (1) | 0.56 | 0.62 |
| Rf value (2) | 0.28 | 0.37 |

The solvent systems used for the silica gel chromatography were n-hexane-ethyl acetate (1:2) and benzene-ethyl acetate (1:1) in (1) and (2), respectively.

The 5057B substance is useful as an antibacterial agent since it has an antibacterial activity.

THE BEST MODE OF CARRYING OUT THE INVENTION

The Streptomyces sp. 5057 strain (FERM-P No. 62) was inoculated into 1 l of a medium (pH 6.0) composed of soluble starch 6.0%, soybean meal 2.5%, beer yeast 0.5%, potassium primary phosphate 0.5%, ammonium sulfate 0.3%, and calcium carbonate 0.3% and cultivation was carried out at 30° C. for 48 hours. The culture broth was inoculated into 100 ml of a medium having the same composition as set forth above and cultivation was carried out with stirring under aeration in a 200-l tank at 30° C. for 96 hours. The rate of aeration was 100 l/min and the rotation rate of the 250 rpm.

The culture broth, after addition of a filter aid (Radiolite 700: registered trademark of Showa Chemical Industry Co.) was filtered to seperate the filtrate and cells. The filtrate was extracted with 40 l of ethyl acetate and the cells with 30 l of acetone. The acetone extract of the cells, concentrated under reduced pressure to remove the acetone, was extracted with 20 l of ethyl acetate. The extract thus obtained was combined with the foregoing extract of the filtrate and the mixture concentrated under reduced pressure. The residue was adsorbed on a column in which 200 g of activated alumina had been packed with the use of ethyl acetate and a mixture of ethyl acetate-ethanol (1:1) passed through the column. Active fractions were concentrated to dryness under reduced pressure to give a mixture of the 5057B and 5057A substances in the state of crude crystals. The mixture thus obtained was applied onto a column in which 500 g of silica gel had been packed with the use of n-hexane-ethyl acetate (1:2) and the same solvent passed through the column. Fractions obtained were subjected to silica gel thin layer chromatography, which was developed with n-hexane-ethyl acetate (1:2). Only elute fractions containing the 5057B substance were collected and concentrated under reduced pressure. The 5057A substance was eluted after the 5057B substance had been eluted. The residue, dissolved in ethyl acetate, was shaken together with dilute hydrochloric acid and then the ethyl acetate layer shaken together with a dilute sodium carbonate solution. The ethyl acetate layer was then concentrated under reduced pressure. Crystals formed were recrystallized from n-hexane-ethyl acetate to give 0.85 g colorless needles of sodium salt of the 5057B substance.

Figure 1:
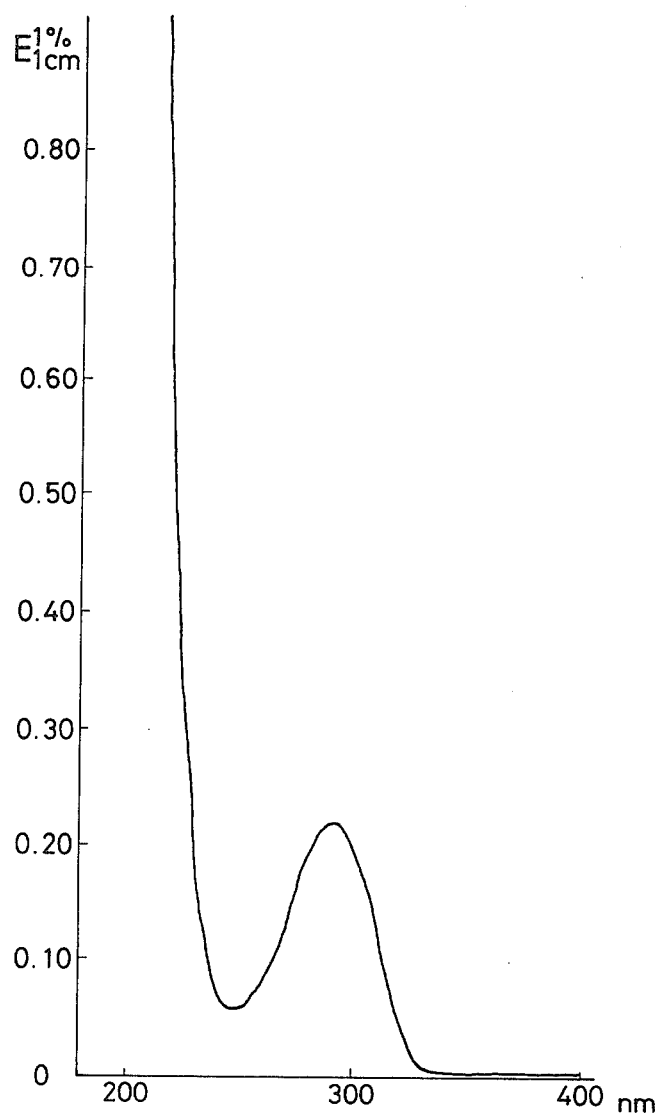
FIG. 1 shows ultraviolet absorption spectrum of sodium salt of the 5057B substance taken in a 0.25% methanol solution, FIG. 2 infrared absorption spectrum of sodium salt of the 5057B substance, and FIG. 3 proton NMR spectrum of sodium salt of the 5057B substance.
Figure 2:
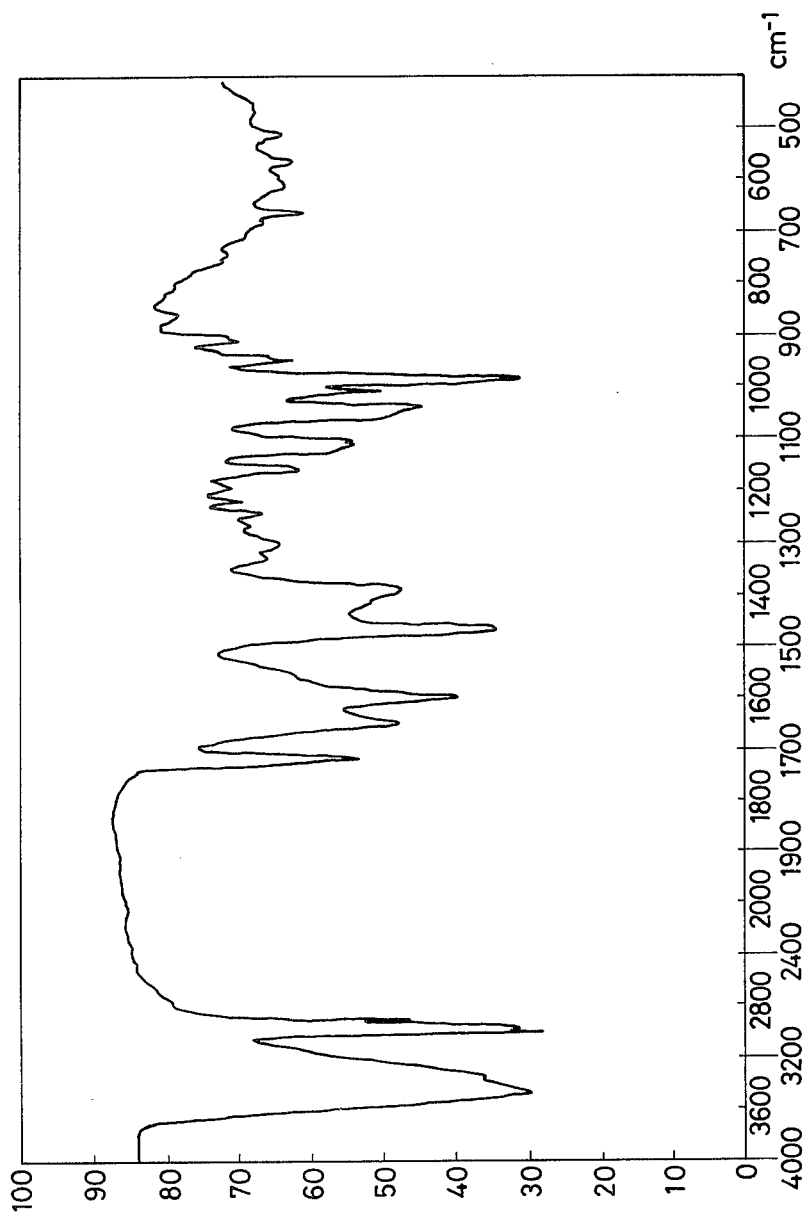
Figure 3:
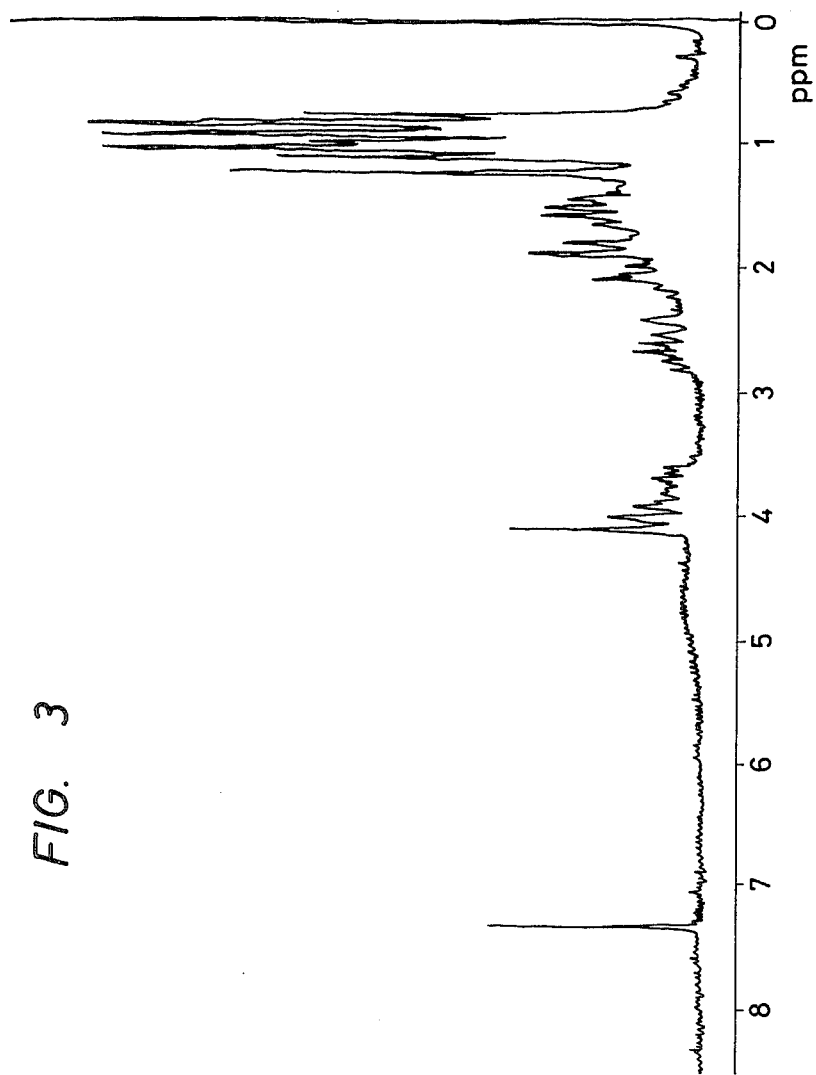

What is claimed is:

1. A new antibiotic 5057B which is itself an acidic substance or the sodium salt thereof which, as the sodium salt, has the following physiochemical properties:
   (1) Colorless needles
   (2) Melting point: 143°-145° C.
   (3) Elementary analysis (Found %): C, 59.96; H, 9.03; O, 27.60; Na, 3.41.
   (4) Specific rotation: $[\alpha]_D^{25} = +5.5°$ (C 1, CHCl$_3$)
   (5) Maximum absorption in ultraviolet absorption spectrum: $\lambda_{max}^{MeOH}$ ($E_{1cm}^{1\%}$) 290 nm (0.88)
   (6) Characteristic absorption (cm$^{-1}$) in infrared absorption spectrum (taken with the potassium bromide tablet: 3480, 3000, 2970, 2812, 1719, 1645, 1595, 1465, 1385, 1160, 1100, 1035, 980
   (7) Solubility: soluble in methanol, ethanol, ethyl acetate, chloroform, ether, acetone, and benzene and so forth; insoluble in water
   (8) Color reaction: positive in the 2,4-dinitrophenylhydrazine reaction; negative in the ninhydrin reaction and the vanilline-sulfuric acid reaction; colors with I$_2$ gas.

2. Antibiotic 5057B according to claim 1 in the form of the sodium salt.

* * * * *

UNITED STATES PATENT AND TRADEMARK OFFICE
CERTIFICATE OF CORRECTION

PATENT NO. : 4,487,762
DATED : December 11, 1984
INVENTOR(S) : Yoko et al.

It is certified that error appears in the above-identified patent and that said Letters Patent are hereby corrected as shown below:

On the title page:
Please change the name of the first-named inventor from Kusakabe Yoko to Yoko Kusakabe.

Signed and Sealed this

Eleventh Day of June 1985

[SEAL]

Attest:

DONALD J. QUIGG

Attesting Officer     Acting Commissioner of Patents and Trademarks